United States Patent

Picone

[11] Patent Number: 5,571,673
[45] Date of Patent: Nov. 5, 1996

[54] METHODS FOR IN-SOLUTION QUENCHING OF FLUORESCENTLY LABELED OLIGONUCLEOTIDE PROBES

[75] Inventor: Teresa K. H. Picone, Benicia, Calif.

[73] Assignee: Hoffmann-La Roche Inc., Nutley, N.J.

[21] Appl. No.: 347,657

[22] Filed: Nov. 23, 1994

[51] Int. Cl.$^6$ .......................... C07H 21/04; C12P 19/34; C12Q 1/68
[52] U.S. Cl. ........................... 435/6; 435/18; 435/91.1; 435/91.2; 536/25.32
[58] Field of Search ........................... 435/6, 91.1, 91.2, 435/18; 536/25.32; 935/77, 78

[56] References Cited

U.S. PATENT DOCUMENTS 5,210,015  5/1993  Gelfand et al. .......................... 435/6

OTHER PUBLICATIONS

Higuchi et al., Nuc. Acids Res. 17(14):5865, 1989.
Kingsbury et al. "Rapid Detection and Identification of Infectious Agents," pp. 245–256, 1985.
Morrison, Nonisotopic DNA Probe Techniques, Academic Press, Inc., 1992, Chapter 13, entitled "Detection of Energy Transfer and Fluorescence Quenching".

*Primary Examiner*—W. Gary Jones
*Assistant Examiner*—Paul B. Tran
*Attorney, Agent, or Firm*—George M. Gould; Dennis P. Tramaloni; Douglas A. Petry

[57] ABSTRACT

The present invention provides methods of detecting a change in the length of an oligonucleotide labeled with a light-emitting label by measuring the light emission in the presence of a DNA binding compound that interacts with the label to modify the light emission of the label, wherein the degree of interaction depends on the length of the oligonucleotide. The methods are applicable in general to nucleic acid sequence detection assays that utilize a reaction that results in the selective cleavage of hybridized oligonucleotide probes, and, in particular, to amplification/detection assays wherein hybridized probes are cleaved concomitant with primer extension.

10 Claims, 3 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

AGAAGGTGAG ATGACCAGAG GACTGAGTCC AAT        33

METHODS FOR IN-SOLUTION QUENCHING OF FLUORESCENTLY LABELED OLIGONUCLEOTIDE PROBES

BACKGROUND OF THE INVENTION

1. Field of the Invention

This invention relates generally to the field of nucleic acid chemistry. More specifically, it relates to methods of decreasing the fluorescence of fluorescently labeled oligonucleotides in solution using a DNA binding compound. Additionally, it relates to methods for detecting degradation of fluorescently labeled single-stranded oligonucleotides in solution. Additionally, the invention relates to methods for detecting nucleic acid sequences by hybridization with a complementary oligonucleotide probe.

2. Description of the Related Art

Nucleic acid detection using oligonucleotide probes has become a standard method for specific target detection. Numerous assay formats have been described. Generally, a nucleic acid sample is hybridized to a labeled target-specific probe, unbound probe is separated from the hybridization duplexes, and the presence of hybridization duplexes are detected using the label. Separation of the hybridized and unhybridized probes can be achieved by a number of means. For example, either the sample nucleic acid may be immobilized on a solid support and the unhybridized probe removed by washing, or the hybridization duplexes and unbound probe may be separated by gel electrophoresis. In general, the methods require a separation step in order that the signal generated following hybridization can be distinguished from the background signal generated by the unbound labeled probe.

Several nucleic acid detection methods have been described which involve selective cleavage of oligonucleotide probes following formation of probe-target hybridization duplexes. Detection of cleaved probes indicates the occurrence of hybridization and, hence, the pence of target sequences. For example, Saiki et al., 1985, *Biotechnology* 3:1008–1012, incorporated herein by reference, describe "oligomer restriction" detection methods, in which hybridization of the target-specific probe generates a restriction site which is then cleaved by the corresponding restriction enzyme. PCT Patent Publication No. WO 89109284, incorporated herein by reference, describes methods in which RNA probes are used to detect DNA target sequences. RNA probes hybridized to DNA target are cleaved using RNaseH, which selectively cleaves RNA in RNA-DNA hybrid duplexes. U.S. Pat. No. 5,210,015, incorporated herein by reference, describes methods which use the 5' to 3' exonuclease activity of a nucleic acid polymerase to cleave probes hybridized to target sequences and thereby release labeled oligonucleotide fragments for detection.

The invention of the polymerase chain reaction (PCR), a process for amplifying nucleic acids, enabled the detection of nucleic acids with greatly increased sensitivity and specificity. Using PCR, segments of single copy genomic DNA can be selectively amplified to an easily detectable level prior to detection. PCR methods are disclosed in U.S. Pat. No. 4,683,202, incorporated herein by reference. PCR and methods for detecting PCR products using an oligonucleotide probe capable of hybridizing with the amplified target nucleic acid are described in U.S. Pat. No. 4,683,195, and European Patent Publication No. 237,362, both incorporated herein by reference.

The methods for detecting nucleic acid described above which involve selective cleavage of hybridization probes following formation of probe-target hybridization duplexes have been applied to the detection of amplified nucleic acid. Saiki et al., 1985, *Science* 230:1350–1353, incorporated herein by reference, describe the application of "oligomer restriction" to the detection of PCR amplified nucleic acid. U.S. Pat. No. 5,210,015, supra, describes the analysis of PCR amplification products using the 5' to 3' exonuclease activity of a nucleic acid polymerase to cleave labeled probes hybridized to target sequences (see also Holland et al, 1991, *Proc. Natl. Acad. Sci. USA* 88:7276–7280, incorporated herein by reference). In the methods of the '015 patent, probes that hybridize to a region of the target nucleic acid bounded by the amplification primers are incorporated into the amplification reaction mixture. Hybridized probes are cleaved by the 5' to 3' nuclease activity of the polymerase during primer extension. Detection of labeled fragments indicates the occurrence of both primer extension and probe hybridization, and, therefore, amplification of the specific target sequence.

A number of agents have been described for labeling nucleic acids, whether probe or target, for facilitating detection of target nucleic acid. Labels have been described that provide signals detectable by fluorescence, radioactivity, colorimetry, X-ray diffraction or absorption, magnetism, and enzymatic activity and include, for example, fluorophores, chromophores, radioactive isotopes (particularly $^{32}$P and $^{125}$I), electron-dense reagents, enzymes, and ligands having specific binding partners. Labeling can be achieved by a number of means, such as chemical modification of a primer or probe to incorporate a label or the use of polymerizing agents to incorporate a modified nucleoside triphosphate into an extension product.

The use of oligonucleotide probes labeled with interacting fluorescent labels in nucleic acid hybridization assays is described in Morrison, 1992, in *Nonisotopic DNA Probe Techniques,* Kricka, ed., Academic Press, Inc., San Diego, Calif., chapter 13; and Heller and Morrison, 1985, in *Rapid Detection and Identification of Infectious Agents,* Academic Press, Inc., San Diego, Calif., pages 245–256; both incorporated herein by reference. The methods rely on the change in fluorescence that occurs when suitable fluorescent labels are brought into close proximity, described in the literature as fluorescence energy transfer (FET), fluorescence resonance energy transfer, nonradiative energy transfer, long-range energy transfer, dipole-coupled energy transfer, or Förster energy transfer.

Morrison, 1992, supra, describes three assay formats. In two of the assay formats, interacting fluorescent labels are bound to separate oligonucleotides that are either brought together or separated by probe hybridization. These assay formats are described as either non-competitive or competitive, depending on whether probe-probe hybridization competes with probe-target hybridization. Both assays formats require the synthesis of two sequence-specific labeled probes. In the third assay format, one fluorescent label is bound to the hybridization probe, and the second fluorescent label is brought into close proximity by intercalating into the double-stranded hybridization duplex. No significant interaction occurs between the intercalating label and the unhybridized probe in solution. Because the intercalating label can intercalate into any double-stranded nucleic acid, this format is practical only for the detection of single stranded target nucleic acid.

U.S. Pat. No. 5,210,015, supra, describes the use of a hybridization probe that is labeled with interacting fluorescent labels in close proximity. The labels are attached such that probe degradation during amplification separates the labels, thereby producing a detectable change in fluorescence. Such multiply-labeled probes are difficult and costly to synthesize.

Conventional techniques of molecular biology and nucleic acid chemistry, which are within the skill of the art, are fully explained fully in the literature. See, for example, Sambrook et al., 1985, *Molecular Cloning—A Laboratory Manual,* Cold Spring Harbor Laboratory, Cold Spring Harbor, N.Y.; *Oligonucleotide Synthesis* (M. J. Gait, ed., 1984); *Nucleic Aria Hybridization* (B. D. Hames and S. J. Higgins. eds., 1984); and a series, *Methods in Enzymology* (Academic Press, Inc.), all of which are incorporated herein by reference. All patents, patent applications, and publications mentioned herein, both supra and infra, are incorporated herein by reference.

SUMMARY OF THE INVENTION

The present invention provides conditions under which significant in-solution quenching by a DNA binding compound of an oligonucleotide labeled with a light-emitting label occurs. This quenching occurs in solution without hybridization of the labeled oligonucleotide to its complementary sequence. The methods of the present invention utilize the dependence of this quenching on the length of the labeled oligonucleotide. The quenching of a short labeled oligonucleotide (about 6 nucleotides or less) is detectably less than the quenching of a longer labeled oligonucleotide. Both the occurrence of in-solution quenching by a DNA binding compound of an oligonucleotide labeled with a light-emitting label and the dependence of the quenching on the length of the oligonucleotide have not been described previously.

The present invention provides methods for detecting the change in length of labeled oligonucleotides based on the change in fluorescence in the presence of a DNA binding compound. In particular, the present invention provides methods for detecting degradation (cleavage) of oligonucleotides in a reaction mixture without the need to separate the cleaved oligonucleotide fragments from the uncleaved oligonucleotide. The oligonucleotides are labeled with a light-emitting label. A DNA binding compound that can interact with the label to quench the light emission of the label is added to the reaction mixture. Oligonucleotide degradation is detected by measuring the light emission of the label following the reaction. Because of the dependence of quenching on the length of the labeled oligonucleotide, oligonucleotide degradation causes a detectable change in the light emission of the labeled oligonucleotide.

The present invention provides improved methods for detecting a target nucleic acid in a sample by hybridization to an oligonucleotide probe. The methods rely on the selective cleavage of probes hybridized to target nucleic acid. Detection of cleaved probes using the methods of the present invention indicates the presence of target nucleic acid.

Thus, the present invention provides a method for detecting a target nucleic acid in a sample, wherein the method comprises:

(a) providing a reaction mixture that comprises the sample and an oligonucleotide probe labeled with a light-emitting label, wherein said probe contains a sequence that is capable of hybridizing to the target nucleic acid, and wherein the DNA binding compound is capable of modifying the light emission of the label;

(b) adding to an aliquot of the reaction mixture of step (a) a DNA binding compound and measuring the light emission of the label;

(c) treating said mixture under conditions under which said oligonucleotide probe hybridizes to said target sequence and is cleaved;

(d) adding to an aliquot of the reaction mixture of step (c) a DNA binding compound and measuring the light emission of the label; and (e) determining if the target sequence is pro,sent by the difference in light emissions measured in step (b) and step (e).

The selective cleavage of probes hybridized to target nucleic acid can be achieved by any of a number of known reactions. Examples of suitable reactions that selectively cleave probes hybridized to a target sequence are described above in Saiki et al, 1985, supra; PCT Patent Publication No. WO 89/09284, supra; and U.S. Pat. No. 5,210,015, supra.

The methods of the present invention for detecting nucleic acids are particularly suited for use in conjunction with amplification processes. Thus, in one embodiment of the invention, the target sequence is amplified prior to, or in conjunction with, step (c).

In a preferred embodiment, the present invention provides improvements to the homogeneous PCR amplification and PCR product detection assay described in U.S. Pat. No. 5,210,015, that use a single nucleic acid polymerase both for primer extension and for cleavage of hybridized labeled probes. The improvements provided by the present invention allow the use of a probe labeled with a single light-emitting label without requiring post-reaction manipulations to separate cleaved and uncleaved probes.

Thus, the present invention provides a method for detecting a target nucleic acid sequence in a sample using a polymerase chain reaction (PCR), wherein the method comprises:

(a) providing a PCR reaction mixture comprising said sample, a pair of oligonucleotide primers, a nucleic acid polymerase having 5' to 3' nuclease activity, and an oligonucleotide probe capable of hybridizing to a region of the target nucleic acid bounded by the oligonucleotide primers, and wherein the probe is labeled with a light-emitting label, and wherein the DNA binding compound is capable of modifying the light emission of the label;

(b) measuring the light emission of the label in the reaction mixture in the presence of a DNA binding compound;

(c) treating the PCR reaction mixture under conditions for PCR, wherein the 5' to 3' nuclease activity of the nucleic acid polymerase cleaves probes hybridized to the target sequence;

(d) measuring the light emission of the label in the presence of a DNA binding compound;

(e) determining if the target sequence is present by the difference in light emission between step (b) and step (d).

DESCRIPTION OF THE PREFERRED EMBODIMENTS

To aid in understanding the invention, several terms are defined below.

The terms "nucleic acid" and "oligonucleotide" refer to probes and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, was well as double- and single-stranded RNA.

The terms "target region", "target sequence", and "target nucleic acid sequence" refer to a region of a nucleic acid which is to be detected.

The term "probe" refers to an oligonucleotide, typically labeled, that forms a duplex structure with a sequence of a target nucleic acid due to complementary base pairing. The probe will comprise a "hybridizing region", preferably consisting of 10 to 50 nucleotides, more preferably 20 to 30 nucleotides, corresponding to a region of the target sequence. "Corresponding" means identical to or complementary to the designated nucleic acid. In the present invention, probe oligonucleotides are labeled with, i.e., bound to, a fluorescent label to enable detection.

The term "hybridization" refers the formation of a duplex structure by two single-stranded nucleic acids due to complementary base pairing. Hybridization can occur between fully complementary nucleic acid strands or between nucleic acid strands that contain minor regions of mismatch. Conditions under which only fully complementary nucleic acid strands will hybridize are referred to as "stringent hybridization conditions". Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs.

The terms "sequence-specific oligonucleotide" and "SSO" refer to oligonucleotide probes wherein the hybridizing region is exactly complementary to the sequence to be detected. The use of stringent hybridization conditions under which the probe will hybridize only to that exactly complementary target sequence allows the detection of the specific target sequence. Stringent hybridization conditions are well known in the art (see, e.g., Sambrook et al 1985, *Molecular Cloning—A Laboratory Manual*, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

The term "subsequence" refers herein to a nucleotide sequence contained within another sequence.

The term "label", as used herein, refers to any atom or molecule which can be attached to a nucleic acid, and which can be used either to provide a detectable signal or to interact with a second label to modify the detectable signal provided by the second label Preferred labels are light-emitting compounds which generate a detectable signal by fluorescence, chemiluminescence, or bioluminescence.

The term "fluorophore" refers to a compound which is capable of fluorescing, i.e. absorbing light at one frequency and emitting light at another, generally lower, frequency.

The term "bioluminescence" refers to a form of chemiluminescence in which the light-emitting compound is one that is found in living organisms. Examples of bioluminescent compounds include bacterial luciferase and firefly luciferase.

The term "quenching" refers to a decrease in fluorescence of a first compound caused by a second compound, regardless of the mechanism. Quenching typically requires that the compounds be in close proximity. As used herein, either the compound or the fluorescence of the compound is said to be quenched, and it is understood that both usages refer to the same phenomenon.

The term "reaction mixture" refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. Reaction mixtures for specific reactions are well-known in the literature.

The present invention provides methods for detecting the change in length of an oligonucleotide labeled with a light-emitting label in solution. The methods of the invention are applicable to the detection of either synthesis or cleavage of oligonucleotides. Detection of the cleaved oligonucleotide is carried out in a solution containing a DNA binding compound that can interact with the label to decrease the light emission of the label. The change in the length of the labeled oligonucleotide from synthesis or cleavage results in a detectable change in the light emission of the attached label. Suitable light-emitting labels and DNA binding compounds that can interact to modify the light mission of the label are described below.

In the exemplified methods of the present invention, the emission of a fluorescent label bound to the single-stranded oligonucleotide is detected. A DNA binding compound quenches the label fluorescence to a degree that depends on the length of the attached oligonucleotide. Both the occurrence of in-solution quenching by a DNA binding compound of a fluorescent label bound to a single-stranded oligonucleotide and the dependence of the quenching on the length of the oligonucleotide are unexpected in view of the prior art.

In a preferred embodiment, the DNA binding agent is polyethylenimine (PEI), which refers to a class of branched or unbranched polymers of ethylenimine of various molecular weights. Derivatives of PEI, such as hydroxyethylated PEI, may be suitable in the present methods. Other compounds which have been demonstrated to work in the methods of the present invention include spermine and spermadine.

Branched PEI is commercially available from Polysciences, Inc. (Warrington, Pa.) in molecular weights, as estimated by viscosity, ranging from 600 up to at least 60,000–80,000. PEI of molecular weights 600, 1200, 1800, 10,000, and 60,000–80,000 have been tested and shown to function in the methods of the present invention to differentiate fluorescently-labeled oligonucleotides of length 2 from those of length 33. One of skill in the art will be able to empirically determine which size of PEI is most suitable for a given application.

Suitable concentrations of the DNA binding compound are determined empirically. Typically, the optimum concentration of DNA binding compound is affected by the type of light-emitting label used and the concentration of reaction reagents. In particular, salt concentration has been observed to affect the optimum concentration of PEI. In some reactions, the addition of a chelator (for example, about 1.5 mM EDTA) into the reaction mixture has been observed to broaden the range of PEI over which the window is near the maximum value. Routine optimization of the concentration of DNA binding compound which provides the maximum difference between the fluorescences of the long and short labeled oligonucleotides can be carried out essentially as described in Examples 1 and 2, below.

Many light emitting compounds described in the art are suitable for use as oligonucleotide labels in the methods of the present invention. Ideally, a fluorophore should have a high Stokes shift (a large difference between the wavelength for maximum absorption and the wavelength for maximum emission) to minimize interference by scattered excitation light. Suitable compounds which are well known in the art include, but are not limited to, fluorescein and derivatives such as FAM, HEX, TET, and JOE; rhodamine and derivatives such as Texas Red, ROX, and TAMRA; Lucifer Yellow, and coumarin derivatives such as 7-Me$_2$N-coumarin-4-acetate, 7 -OH-4-CH$_3$-coumarin-3-acetate, and 7-NH$_2$-4-CH$_3$-coumarin-3-acetate (AMCA). FAM, HEX, TET, JOE, ROX, and TAMRA are marketed by Perkin Elmer, Applied Biosystems Division (Foster City, Calif.). Texas Red and many other suitable compounds are marketed by Molecular Probes (Eugene, Oreg.). Examples of chemiluminescent and bioluminescent compounds that may be suitable for use as the energy donor include luminol (aminophthalhydrazide) and derivatives, and Luciferases.

An oligonucleotide can be prepared by any suitable method, including, for example, cloning and isolation of appropriate sequences using restriction enzymes and direct chemical synthesis by a method such as the phosphotriester method of Narang et al 1979, *Meth. Enzymol.* 68:90–99; the phosphodiester method of Brown et al 1979, *Meth. Enzymol.* 68:109–151; the diethylphosphoramidite method of Beaucage et al 1981, *Tetrahedron Lett.* 22:1859–1862; and the solid support method of U.S. Pat. No. 4,458,066, each incorporated herein by reference. Methods for synthesizing labeled oligonucleotides are described in Agrawal and Zamecnik, 1990, *Nucl. Acids. Res.* 18(18):5419–5423; MacMillan and Verdine, 1990, *J. Org. Chem.* 55:5931–5933; Pieles et al 1989, *Nucl. Acids. Res.* 17(22):8967–8978; Roger et al 1989, *Nucl. Acids. Res.* 17(19):7643–7651; and Tesler et al 1989, *J. Am. Chem. Soc.* 111:6966–6976, each incorporated herein by reference. A review of synthesis methods is provided in Goodchild, 1990, *Bioconjugate Chemistry* 1(3):165–187, incorporated herein by reference.

The methods of the present invention are particularly suitable for the detection of amplified nucleic acids, either DNA or RNA. Suitable amplification methods in addition to the PCR (U.S. Pat. Nos. 4,683,195; 4,683,202; and 4,965,188) include, but are not limited to, the following: Ligase Chain Reaction (LCR, Wu and Wallace, 1989, *Genomics* 4:560–569 and Barany, 1991, *Proc. Natl. Acad. Sci. USA* 88:189–193); Polymerase Ligase Chain Reaction (Barany, 1991, *PCR Methods and Applic.* 1:5–16); Gap-LCR (PCT Patent Publication No. WO 90/01069); Repair Chain Reaction (European Patent Publication No. 439,182 A2), 3SR (Kwoh et al 1989, *Proc. Natl. Acad. Sci. USA* 86:1173–1177; Guatelli et al 1990, *Proc. Natl. Acad. Sci. USA* 87:1874–1878; PCT Patent Publication No. WO 92/0880A), and NASBA (U.S. Pat. No. 5,130,238). All of the above references are incorporated herein by reference. This invention is not limited to any particular amplification system. As other systems are developed, those systems may benefit by practice of this invention. A recent survey of amplification systems was published in Abramson and Myers, 1993, *Current Opinion in Biotechnology* 4:41–47, incorporated herein by reference.

A preferred embodiment of the invention provides improvements to the process described in U.S. Pat. No. 5,210,015, supra, and Holland et al., 1991, *Proc. Natl. Acad. Sci. USA* 88:7276–7280, incorporated herein by reference. The process uses the 5' to 3' exonuclease activity of a thermostable DNA polymerase to cleave annealed labeled oligonucleotide probes from hybridization duplexes and release labeled fragments for detection. Cleavage of the labeled probes of the present invention by the 5' to 3' exonuclease activity of the DNA polymerase frees the labels into the reaction mixture. The in-solution signal quenching by the DNA binding compound is significantly greater when the fluorophore is bound to the full-length uncleaved oligonucleotide probe than when bound to the shortened cleaved fragment. The resulting increase in observed fluorescence indicates probe cleavage, which necessarily indicates both the presence of target sequences and the occurrence of probe/target hybridization.

In general, the nucleic acid in the sample will be a sequence of DNA, most usually genomic DNA. However, the present invention can also be practiced with other nucleic acids, such as messenger RNA, ribosomal RNA, viral RNA, or cloned DNA. Suitable nucleic acid samples include single or double-stranded DNA or RNA for use in the present invention. Those of skill in the art will recognize that, depending on which reaction is used to cleave the labeled oligonucleotide probes, whatever the nature of the nucleic acid, the nucleic acid can be detected merely by making appropriate and well recognized modifications to the method being used.

Sample preparation will vary depending on the source of the sample, the target to be detected, and the oligonucleotide-degrading reaction used in the assay. Each assay requires a target sample in a buffer that is compatible with the assay reagents. If the target is amplified either before or simultaneously with detection of probe cleavage, the target nucleic acid must be in a buffer compatible with the enzymes used to amplify the target. The target nucleic acid can be isolated from a variety of biological materials including tissues, body fluids, feces, sputum, saliva, plant cells, bacterial cultures, and the like.

Sample preparation methods suitable for each assay are described in the an (see, for example, Sambrook et al., supra). Simple and rapid methods of preparing samples for the PCR amplification of target sequences are described in Higuchi, 1989, in *PCR Technology* (Erlich ed., Stockton Press, New York), and in *PCR Protocols,* Chapters 18–20

(Innis et at., ed., Academic Press, 1990), both incorporated herein by reference. One of skin in the an will be able to select and empirically optimize a suitable protocol.

The light emission of a label in a solution is measured in a spectrofluorometer, such as a Hitachi/Perkin Elmer Model 650-40 (Perkin Elmer, Norwalk, Conn.) or a PTI LS-100 Luminescence Spectrophotometer (Photon Technology International, London, Ontario, Canada). A spectrofluorometer, depending on the features of the particular machine utilized, offers the opportunity to set the excitation and emission wavelength, as well as bandwidth. One of ordinary skill in the art will know how to determine the wavelength and bandwidth settings appropriate for detecting the light emission from a particular label. General guidance is found in, for example, *The Merck Index*, (eds. Budavari et al., 1989, Merck Co. Inc. Rahway, N.J.) and the *Molecular Probes, Inc.* (Eugene, Oreg.) *Catalog*, 1990, by Haugland, both incorporated herein by reference. Although each label has a discrete light emission spectrum, a broad range of detection wavelengths are suitable for practicing the invention.

The change in light emission resulting from probe cleavage preferably is measured by comparing the light emission measured before and after probe cleavage. Alternatively, the change in light emission can be measured concurrent with probe-cleavage by incorporating the DNA binding agent into the reaction mixture and monitoring the probe fluorescence continuously or intermittently while the reaction is carried out. In this case, the use of reaction vessels which are also suitable for use in measuring light emission, which allows direct measurements of light-emission without the need to open the reaction vessel, is preferred. However, as particular DNA binding agents may inhibit particular probe-cleaving reactions, it may be necessary to omit the DNA binding agent from the reaction mixture. In this case, "pre-reaction" measurements can be carried out using a duplicate reaction mixture. Typically, the reaction mixture is divided prior to carrying out the reaction, and a portion of the reaction mixture which is not subject to the reaction conditions is used for the pre-reaction emission measurements. Typically, it is most convenient to measure both the pre-reaction light emission and the post-reaction light emission after completion of the reaction.

In preferred methods in which the nucleic acid detection method is combined with PCR amplification, as described above, the amplification reaction is carried out as an automated process. Thermal cyclers are currently available from Perkin Elmer (Norwalk, Conn.) that uses a heat block capable of holding up to 48 or 96 reaction tubes. Consequently, up to 96 amplification reactions can be carried out simultaneously.

Suitable optical systems for measuring the light emission from all tubes in a PCR amplification are described in Higuchi et al., 1992, supra, Higuchi et al., 1993, supra, and copending and commonly assigned U.S. Ser. No. 08/266, 061 and European Patent Publication No. 512,334, each incorporated herein by reference. In one such optical system, multiple fiber optic leads are used to transmit the excitation light from the source to the reaction tube and measures the emission light from each tube. Only a single spectrofluorometer is needed to read fluorescence from the reaction tubes, as each fiber optic can be read rapidly one at a time. An alternative optical system uses a video camera to measure the fluorescence of multiple reaction vessels simultaneously. It will be obvious to one of skill in the art that the alternative detection apparatuses described in the '168 application also are adaptable to the present methods.

An alternative suitable detection scheme uses a 96-well microtiter format. This type of format is frequently desirable in clinical laboratories for large scale sample screening, for example, for genetic analysis such as screening for sickle-cell anemia or the AIDS virus in blood bank screening procede. The present invention is suitable for this type of analysis and eliminates the need for the numerous washing and extraction procedures that are required with known "in-well" assay procedures such as ELISA type formats or other optical density-based methods. (See Kolber et al., 1988, *J. Immun. Meth.* 108:255–264, Huschtscha et al 1989, *In Vitro Cell and Dev. Biol.* 25(1):105–108, and Vollet et al., 1979, *The Enzyme Linked Immunosorbent Assay,* Dynatech Labs, Alexandria, Va.). The present detection methods also allow direct light emission measurement using an apparatus similar to ELISA plate reader, but designed to excite and measure fluorescence. For example, the CytoFluor™ 2300 machine manufactured by Millipore (Bedford, Mass.) is suitable in such a method.

It will be obvious to one skilled in the art that the methods of the present invention are not limited to a particular detection method, thermal cycler or signal measuring machines, or number of reaction vessels.

The methods of the present invention can be used to simultaneously detect multiple target sequences. Probes specific to each target are present in the reaction mixture. For each target nucleic acid present in the sample, the corresponding probe will hybridize and be cleaved. In order to detect the cleaved probes separately, each species of probe is labeled with a label that emits light at a delectably distinct wavelength. Each species of probe is then detected separately by suitable selection of the measured wavelength.

Thus, the methods of the present invention are useful for detecting the amplification products in PCR co-amplification methods for detecting several targets in one sample. The invention is particularly useful for quantitative comparisons of two different nucleic acid targets in the same sample. Methods for quantitating nucleic acids are described in U.S. Pat. No. 5,219,727, incorporated herein by reference. The quantitation methods described are PCR-based methods using an internal standard to determine either the relative amount of a target or accurately quantitate the amount of target present prior to amplification, respectively.

The differential quenching of short and long labeled oligonucleotides may also be used to measure the incorporation of nucleotides into a synthesized oligonucleotide. For example, DNA polymerase activity assays measure the rate of incorporation of nucleotides. To measure the incorporation of nucleotides, a reaction mixture is provided containing labeled dNTPs in addition to the other reagents necessary for oligonucleotide synthesis, such as a DNA polymerase in a suitable buffer. The fluorescence of the reaction mixture prior to synthesis is measured in the presence of a DNA binding compound. Prior to synthesis, all labels are bound to single nucleotides and quenching is minimal. Following synthesis, the fluorescence of the reaction mixture is measured in the presence of the DNA binding compound. The synthesis of oligonucleotides malts in a decrease in mount of labeled nucleotides. Because the longer, newly synthesized oligonucleotides are more effectively quenched by the DNA binding compound, the incorporation of dNTP into oligonucleotides results in a reduction of fluorescence.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Length-dependent Quenching by PEI

This example describes the length-dependent quenching of labeled oligonucleotides in solution. Oligonucleotides of length 33 and length 2 were labeled with one of a variety of fluorescent labels and the fluorescence of each oligonucleotide was measure in a solution containing PEI. The measurements were repeated using solutions containing various concentrations of PEI in order to determine the optimal concentration of PEI for which the difference in signal between the oligonucleotides of length 33 and 2 is maximized.

Probes were synthesized on an ABI 394 DNA synthesizer (Perkin Elmer ABD, Foster City, Calif.) at a 1 micromole scale. Amidites of the fluorescent label were used during oligonucleotide synthesis to provide a 5'-labeled oligonucleotide directly. Probes of length 33 were synthesized with a $PO_4$ group at the 3' end, for use in the methods described in Example 2. The nucleic acid sequence of each of the labeled probes of length 33 was SK535 (SEQ ID NO: 1) 5'-AGAAGGTGAGATGACCAGAGGACTGAGTCCAAT. The nucleic acid sequence of the probes of length 2 consisted of 5'-AG, which corresponds to a degradation product of the probes of length 33.

The fluorescent labels used are listed below, along with the excitation and emission wavelengths for each of the labels are shown below. The slit width of the filter used for the detection of each label, as described below, also is indicated.

| Label | Filters Used For Fluorescence Measurements (wavelength and width shown in nanometers) | |
|---|---|---|
| | Excitation Maximum | Emission Maximum |
| fluorescein (FAM) | 485 (20) | 530 (25) |
| hexachlorofluorescein (HEX) | 530 (25) | 590 (35) |
| dichlorodimethylfluorescein (JOE) | 490 (40) | 580 (50) |
| rhodamine (ROX) | 590 (40) | 645 (40) |
| tetramethylrhodamine (TAMRA) | 560 (20) | 620 (40) |

For each of the probes listed below, replicate assay solutions containing 1 µM of probe in 50 µl of buffer (50 mM Bicine, 100 mM KOAc (pH 8.3), 3.6 mM $Mn(OAc)_2$) were added to the wells of microtiter plates. A series of solutions containing PEI (molecular weight 1200, from Polysciences Inc., Warrington, Pa.) at concentrations of 0.016%, 0.008%, 0.004%, 0.002%, and 0.001%, were prepared. A 50 µl volume of water was added to one well to be used as a maximum signal control. A 50 µl of PEI solution were added to each of the remaining wells. Fluorescence measurements were carried out in a Millipore Cytofluor 2300 Microtiter plate reader using the excitation and emission wavelengths provided in the table, above.

The methods of the present invention rely on the difference in the quenching of short and long labeled oligonucleotides. A measure of this difference in quenching, referred to a "window", was calculated from the individual fluorescence measurements as follows. Firstly, the "background" level of quenching resulting from the buffer alone was measured and subtracted from each probe fluorescence measurement. Secondly, residual fluorescence was calculated as the ratio of the fluorescence of a probe in the presence of PEI to the fluorescence of the same probe without PEI, and expressed as a per cent of the unquenched fluorescence. Finally, the window was calculated as the difference between the residual fluorescence of the labeled oligonucleotide of length 2 and the residual fluorescence of the oligonucleotide of length 33. The window is a measure of the change in signal which would result from the degradation of labeled probes of length 33 into fragments of length 2. A PEI concentration which provides the maximum window provides the greatest sensitivity in the detection methods of the present invention.

Figure 1:
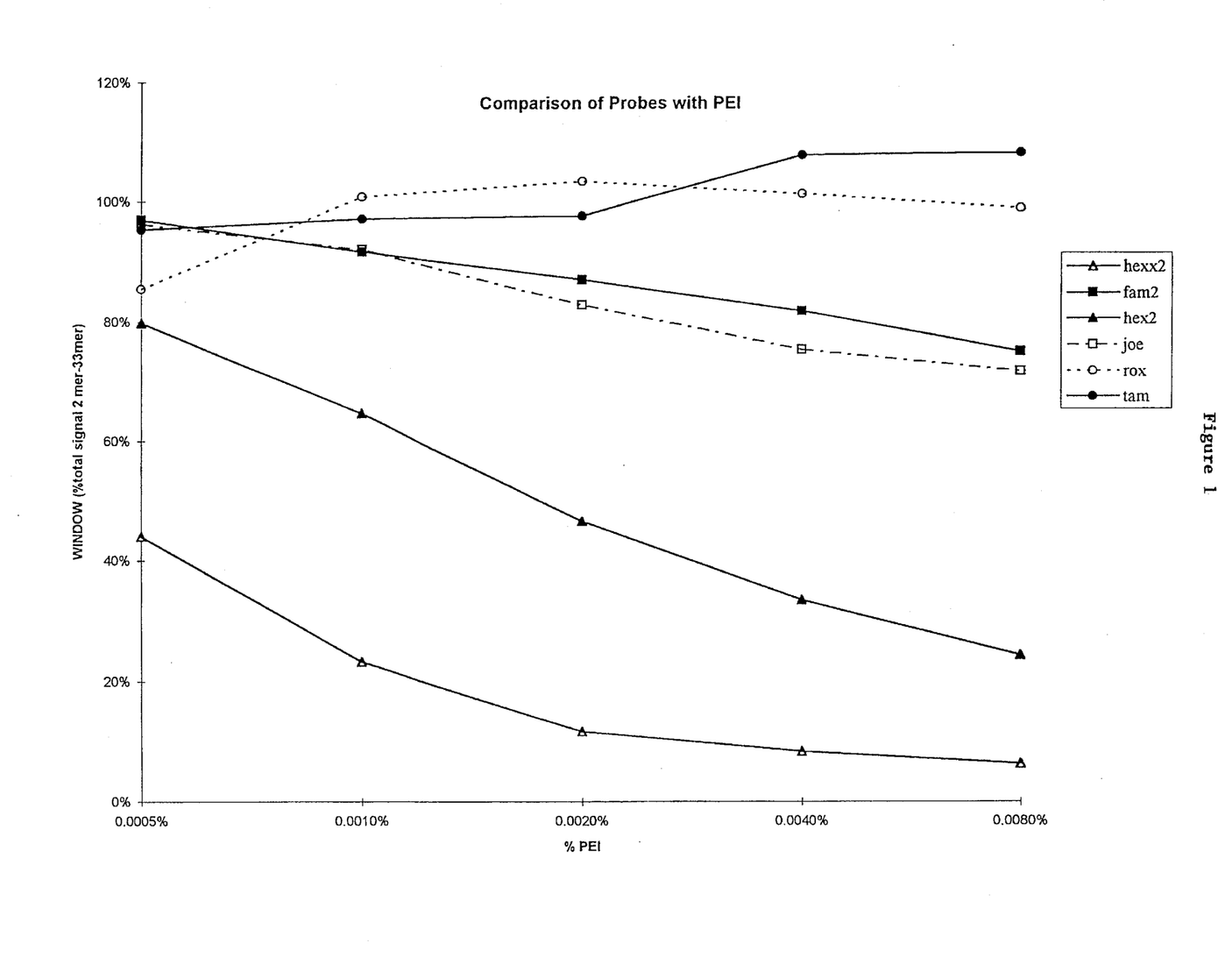
FIG. 1 relates to the dependence of quenching on the length of the labeled oligonucleotide, the light-emitting label, and the concentration of the DNA binding compound, as described in Example 1.

The results are presented in FIG. 1, wherein the windows obtained using the various probe labels are plotted relative to the concentration of PEI. The line designations refer to oligonucleotides labeled as follows:

hexx2: HEX-labeled oligonucleotides, wherein the label is attached to the 5' end of the oligonucleotides through a spacer.

fam2: FAM-labeled oligonucleotides.

hex2: HEX-labeled probes, wherein the label is attached directly to the 5' end of the oligonucleotides.

joe: JOE-labeled oligonucleotides.

rox: ROX-labeled oligonucleotides.

tam: TAMRA-labeled oligonucleotides.

As can be seen from FIG. 1, a significant window was observed with each label at some concentration of PEI. The size of the window obtained depended both on the label and the concentration of PEI. Attachment of a HEX label to the oligonucleotide through a spacer was observed to decrease the size of the window obtained within the tested range of PEI concentrations.

EXAMPLE 2

The Effect of PEI Molecular Weight

In this example, the effect of the molecular weight and concentration of the PEI on the quenching of fluorescently-labeled probes are described. Experiments essentially as described in Example 1 were carried out using the FAM-labeled oligonucleotides but using PEI of various sizes and over a larger concentration range than in Example 1.

PEI with molecular weights of 600, 1200, 1800, and 10,000 kilodalton were obtained from Polysciences Inc., Warrington, Pa. Emission measurements were carried out in assay solutions containing buffer consisting of 50 mM Bicine, 115 mM KOAc (pH 8.3), and 8% glycerol. For each size PEI, the PEI was incorporated into the assay solutions in concentrations of from 0.000013% to 0.02% (w/v). For each PEI size and concentration, the window was calculated as in Example 1.

Figure 2:
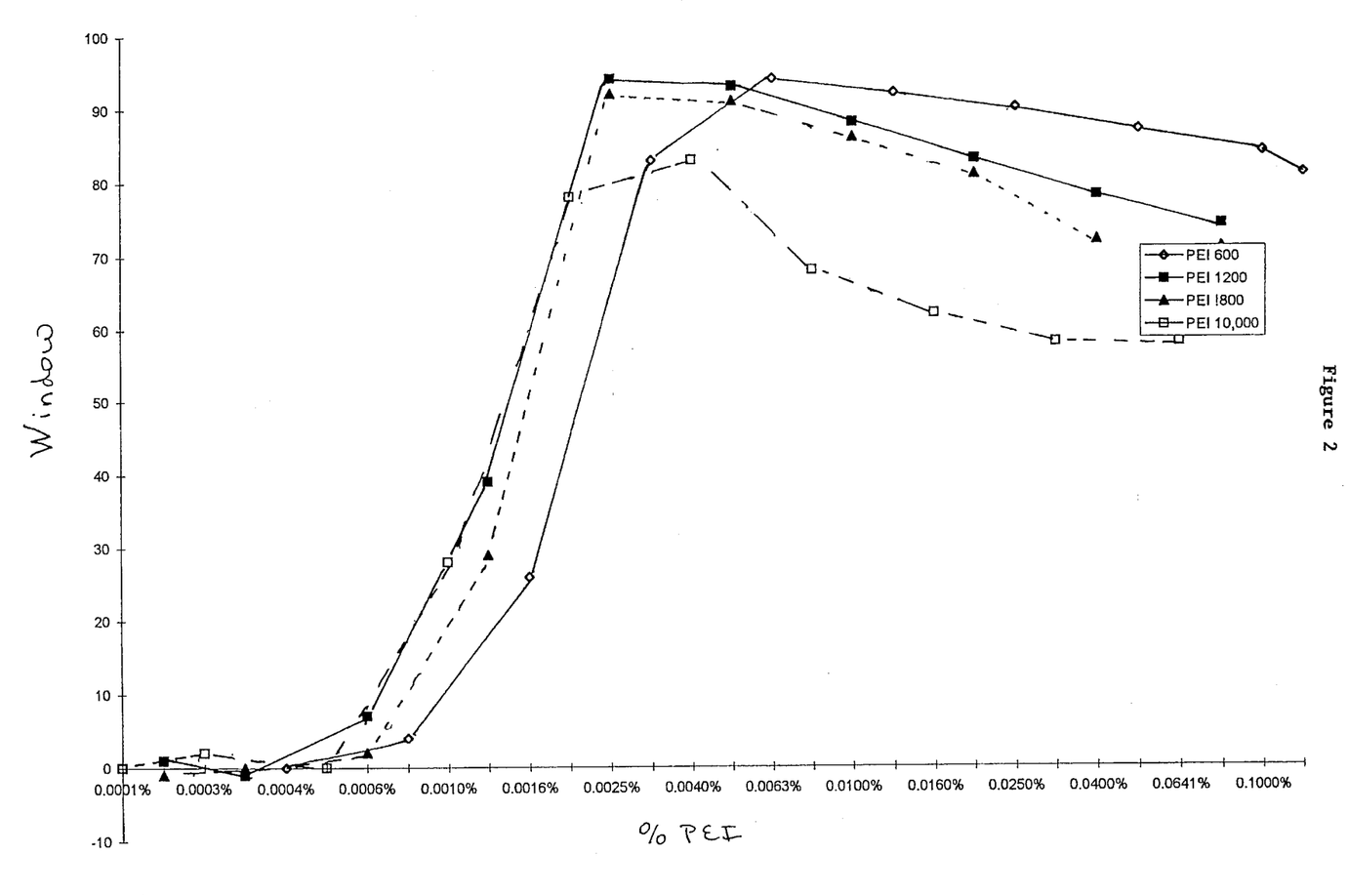
FIG. 2 relates to the dependence of quenching on the molecular weight and concentration of PEI used, as described in Example 2.

The results are presented in FIG. 2. Each size of PEI was seen to function in the methods of the present invention, although minor differences in window size were obtained using the different sizes of PEI. For each size of PEI, the optimal PEI concentration can be determined from FIG. 2 as the PEI concentration which provides the largest window. The above experiment exemplifies the routine optimization of PEI size and concentration which one of skill in the art would carry out for each detection assay.

EXAMPLE 3

Quantitation by PCR Amplification

This example describes the quantitation of a nucleic acid using the methods of the present invention. In this example, an target consisting of hepatitis C virus (HCV) RNA was amplified by an RT-PCR in the presence of fluorescently labeled probes. The exonuclease activity of the DNA polymerase cleaved labeled probes hybridized to the target sequence downstream from an amplification primer, thereby releasing small labeled oligonucleotide fragments of the probe into the reaction mixture. Following amplification, PEI was added to the reaction mixture and the fluorescence of the labeled probes measured. The generation of short labeled oligonucleotide degradation products results in an increase in the measured fluorescence because the degradation products are not quenched by the PEI as much as full-length, undegraded probe. Because probe degradation occurs concomitant with target amplification, the increase in fluorescence indicates amplification of the target sequence.

A quantitative estimate of the initial target sequence copy number was obtained by comparing the increase in fluorescence resulting from the amplification of the target sequence to the increase in fluorescence obtained from the amplification of a second nucleic acid sequence. The second nucleic acid sequence is added to a reaction in a known copy number, thereby providing a internal quantitation standard (IQS) to which the amplification of the unknown sample is compared. Detection of the second nucleic acid sequence is achieved using a second fluorescent label which emits light at a distinct wavelength.

Amplification

Two target RNA sequences were amplified in each reaction. Both target nucleic acid sequences were simultaneously amplified using a single primer pair, KY78 and KY80. In this example, the target RNA sequences were generated from transcription plasmids. The construction and use of a transcription plasmid containing an HCV sequence, the amplification primers, and the RT-PCR amplification are described in Young et al., 1993, *J. Clin. Microbiol.* 31(4):882–886, incorporated herein by reference. The first target sequence consisted of a region from the HCV 5' non-coding region. The second target nucleic acid sequence, which is used as an IQS, comprises the same two primer binding sites flanking a nucleic acid sequence which contains an alternate probe binding site. Consequently, both target sequences are amplified using the same primer pair, but the two target sequences can be detected independently using different sequence-specific probes. The construction and use of an IQS is described in Mulder et al., 1994, *J. Clin. Microbiology* 34(2):292–300, incorporated herein by reference.

Amplifications were carried out in the presence of both a FAM-labeled probe specific for the HCV target sequence and a HEX-labeled probe specific for the IQS. The emission maxima of the FAM and HEX are at different wavelengths, which permits independent detection of the probes by suitable selection of the measured frequency. The nucleic acid sequences of the probes are shown in the 5' to 3' orientation. The probes were synthesized with the labels at the 5' end, as described above. Each probe was synthesized to have a 3'—$PO_4$ instead of a 3'—OH to block any extension by Taq polymerase during the amplification reaction. The sequence of the FAM-labeled probe for the detection of the HCV target sequence was described in Young et al., 1993, supra, as KY88. The sequence of the HEX-labeled probe for the detection of the IQS is provided in Example 1, above (SEQ ID NO: 1).

Amplifications were carried out in 100 μl reactions containing the following reagents:

HCV target sequence (copy number as described below)

1000 copies of the IQS 50 mM Bicine 100 mM KOAc, pH 8.3

3.6 mM Mn(OAc)2

0.4 μM each palmer

1 μM each probe 0.2 mM each dUTP, dATP, dGTP, dCTP 20 units rTth DNA polymerase*

2 units Amperase Uracil-N-Glycosolase*

8% Glycerol * Developed and manufactured by Hoffmann-La Roche and marketed by Perkin Elmer, Norwalk, Conn.

Amplifications were carried out using from 0 to $10^7$ copies of HCV target. In addition to the reaction mixtures subjected to PCR thermal cycling conditions, two additional reaction mixtures were made and stored (no temperature cycling) for use as measurement controls. Reaction mixtures were subjected to the following amplification scheme in a GeneAmp 9600 Thermal Cycler (Perkin Elmer, Norwalk, Conn.):

50° C. for 2 minutes
60° C. for 30 minutes
95° C. for 1 minute
2 cycles:
95° C. for 15 seconds
60° C. for 20 seconds
46 cycles:
90° C. for 15 seconds
60° C. for 20 seconds
72° C. for at least 5 to 10 minutes, up to 1 hour Following amplification, reactions are held at 4° C. until analyzed.

Analysis

Fifty μl of 0,004% PEI (molecular weight 1200) solution containing 0.8 mM EDTA were added to 50 μl of each reaction mixture following amplification and also to one of the two control reaction mixtures not subject to amplification conditions. The fluorescence was measured in a CytoFluor™ 2300 (Millipore, Location) microtiter plate reader. The fluorescence of FAM-labeled probes was measured at room temperature using a 485 nm excitation filter (20 nm band pass width) and 530 nm emission filter (25 nm band pass width). The fluorescence of HEX-labeled probes was measured at room temperature using a 530 nm excitation filter (25 nm band pass width) and 590 nm emission filter (35 nm band pass width).

Figure 3:
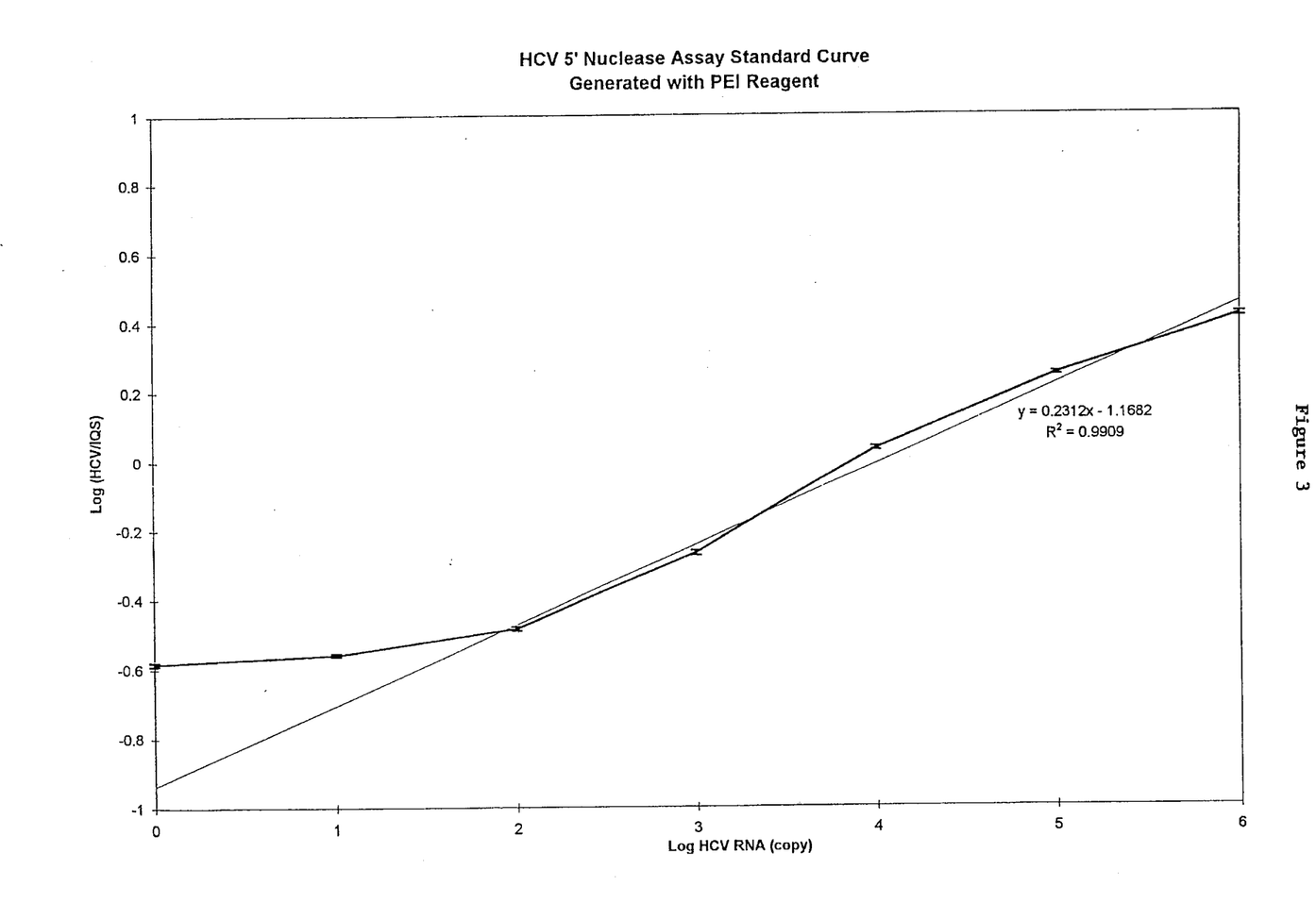
FIG. 3 relates to quantitation of nucleic acids by amplifying a target nucleic acid sequence in the presence of an internal quantity control standard, as described in Example 3.

The measured fluorescence of each probe label was corrected by subtracting the fluorescence of an uncycled reaction mixture without probe, both measured at the wavelength appropriate for the label. The results are presented in FIG. 3, plotted as the logarithm (log) of the ratio of the fluorescences (HCV/IQS) versus the log of the HCV target copy number. A "standard curve" was generated by a least-squares linear fit of the data.

The standard curve generated from the above experiment allows the quantitation of unknown HCV samples. For quantitation of an unknown HCV sample, the HCV nucleic acid is amplified with a known amount of IQS as described above. The log of the ratio of the measured changes in fluorescence is calculated, and the corresponding HCV copy number is determined from the equation of the standard curve.

---

I claim:

1. A method for detecting a change in length of an oligonucleotide labeled with a light-emitting label, wherein the change in length is catalyzed by a reaction carried out in a reaction mixture, and wherein said method comprises:

(a) measuring the light emission of said label in said reaction mixture in the presence of a DNA binding compound that is capable of interacting with said label to modify the light emission of said label, wherein the interaction depends on the length of said oligonucleotide, and wherein said DNA binding compound is selected from the group consisting of polyethylenimine, hydroxyethylated polyethylenimine, spermine, and spermadine;

(b) carrying out said reaction in said reaction mixture under conditions which result in a change in length of said oligonucleotide;

(c) measuring the light emission of said label in said reaction mixture in the presence of said DNA binding compound; and (d) detecting the change in length of said oligonucleotide by comparing the light emission measured in step (a) to the light emission measured in step(c), wherein a change in light emission indicates a change in length of said oligonucleotide.

2. The method of claim 1, wherein said compound is polyethylenimine.

3. The method of claim 2, wherein said label is selected from the group consisting of fluorescein, rhodamine, and derivatives thereof.

4. A method for detecting a target nucleic acid in a sample, wherein the method comprises:

(a) providing a reaction mixture for a reaction, wherein said reaction mixture comprises said sample and a single-stranded oligonucleotide probe labeled with a light-emitting label, wherein said probe contains a sequence that is capable or hybridizing to said target nucleic acid, and wherein said reaction catalyzes the cleavage of said oligonucleotide only if said oligonucleotide is hybridized to said target nucleic acid;

(b) measuring the light emission of said label in said reaction mixture in the presence of a DNA binding compound that is capable of modifying the light emission of said label, wherein the interaction depends on the length of said oligonucleotide, and wherein said DNA binding compound is selected from the group consisting of polyethylenimine, hydroxyethylated polyethylenimine, spermine, and spermadine:

(c) treating said mixture under conditions under which said oligonucleotide probe hybridizes to said target sequence and is cleaved;

(d) measuring the light emission of said label in said reaction mixture in the presence of said DNA binding compound; and (e) determining if the target sequence is present by comparing the light emission measured in step (b) to the light emission measured in step(d), wherein a change in light emission indicates that the target sequence is present.

5. The method of claim 4, wherein said target sequence is amplified prior to step (d).

6. The method of claim 4, wherein said compound is polyethylenimine.

7. The method of claim 6, wherein said label is selected from the group consisting of fluorescein, rhodamine, and derivatives thereof.

8. A method for detecting a target nucleic acid sequence in a sample using a polymerase chain reaction (PCR), wherein the process comprises:

(a) providing a PCR reaction mixture comprising said sample, a pair of oligonucleotide primers, a nucleic acid polymerase having 5' to 3' nuclease activity, and an oligonucleotide probe capable of hybridizing to a region of said target nucleic acid, wherein said oligonucleotide probe hybridizes within said target nucleic acid sequence bounded by said oligonucleotide primers, and wherein said oligonucleotide probe is labeled with a light-emitting label;

(b) measuring the light emission of said label in said reaction mixture in the presence of a DNA binding compound that is capable of modifying the light emission of said label, wherein the interaction depends on the length of said oligonucleotide, and wherein said DNA binding compound is selected from the group consisting of polyethylenimine, hydroxyethylated polyethylenimine, spermine, and spermadine;

(c) treating the PCR reaction mixture under conditions for PCR, wherein the 5' to 3' nuclease activity of the nucleic acid polymerase cleaves probes hybridized to the target sequence;

(d) measuring the light emission of said label in said reaction mixture in the presence of said DNA binding compound; and (e) determining if the target sequence is present by comparing the light emission measured in step (b) to the light emission measured in step(d), wherein a change in light emission indicates that the target sequence is present.

9. The method of claim 8, wherein said DNA binding compound is polyethylenimine.

10. The method of claim 9, wherein said label is selected from the group consisting of fluorescein, rhodamine, and derivatives thereof.

* * * * *